United States Patent [19]

Lo et al.

[11] Patent Number: 4,610,819

[45] Date of Patent: Sep. 9, 1986

[54] PROCESS FOR THE PREPARATION OF AROMATIC-1,4-OXAZEPINONES AND THIONES

[75] Inventors: Young S. Lo, Richmond; Albert D. Cale, Jr., Mechanicsville, both of Va.

[73] Assignee: A. H. Robins Company, Inc., Richmond, Va.

[21] Appl. No.: 652,017

[22] Filed: Sep. 19, 1984

[51] Int. Cl.$^4$ ............... C07D 267/14; C07D 281/10; C07D 498/04; C07D 513/04; C07D 413/06; C07D 417/06

[52] U.S. Cl. ............... 540/488; 546/329; 548/378; 540/490; 548/341; 548/561; 548/567; 544/128; 564/163; 564/161; 544/124; 564/165; 544/169; 564/166; 564/167; 544/363; 564/170; 564/172; 544/365; 564/180; 564/183; 544/400; 562/433; 562/466; 546/156; 562/467; 546/155; 562/465; 546/193; 514/214; 546/194; 546/275; 546/262; 546/263; 546/276; 546/278; 546/279; 546/291; 546/290; 546/296; 546/297; 546/298; 546/307; 546/308; 546/310; 546/316; 546/318; 546/323; 546/326; 546/246; 546/247

[58] Field of Search ............... 260/239.3 B, 239.3 T

[56] References Cited

FOREIGN PATENT DOCUMENTS 107930 9/1984 European Pat. Off. ..... 260/239.3 T

Primary Examiner—Robert T. Bond

[57] ABSTRACT

A process for the preparation of 1,4-oxazepinones and thiones having the formula:

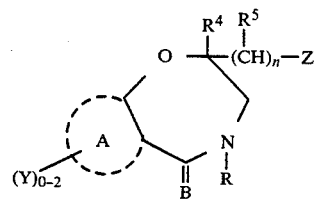

wherein A is an aromatic ring selected from benzene, naphthalene, quinoline or pyridine; n is 1 to 3; Z is an amino radical; R is hydrogen, loweralkyl, cycloalkyl or phenylloweralkyl; and $R^4$ and $R^5$ are hydrogen and loweralkyl starting from chloroaromatic carboxylates and alkanolamines is disclosed.

6 Claims, No Drawings

PROCESS FOR THE PREPARATION OF AROMATIC-1,4-OXAZEPINONES AND THIONES

BACKGROUND OF THE INVENTION

1. Field of Invention

The present invention relates to a novel process for the preparation of aromatic 1,4-oxazepinones and thiones which have the aromatic component fused into the oxazepine component, each component thereby having two commonly shared carbon atoms and the oxazepine ring having an oxo or thioxo function on the carbon atom adjacent to one of the shared carbon atoms and its carbon atom three positions away from the oxo or thioxo function substituted by a short chain aminoalkyl or heterocyclicaminoalkyl radical and novel chemical intermediates therefor. The process utilizes haloaromatic carboxylates in reaction with certain alkanolamines. The oxazepinones and oxazepinethiones prepared by the process have utility as anti-histaminics with low sedative potential.

2. Information Disclosure Statement

The above and below described aromatic-1,4-oxazepinones and thiones generally preparable by the process of the present invention are also disclosed in a U.S. patent application filed on even date, which is a continuation-in-part application of U.S. application Ser. No. 527,559 filed Aug. 29, 1983, now abandoned. In that application the compounds are formed by a rearrangement reaction starting with, for example, a pyrrolidinyloxy aromatic carboxylic acid chloride or by the method of the present invention.

OBJECTS AND SUMMARY OF THE INVENTION

The oxazepinone and oxazepinethione derivatives preparable by the process of the present invention have the formula:

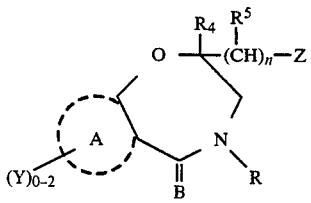

Formula I wherein;

A represents an aromatic ring having two of its carbon atoms held mutually with the oxazepine moiety selected from the group consisting of benzene, naphthalene, quinoline or pyridine, any of the rings optionally substituted by one or two Y radicals selected from the group consisting of halo, loweralkyl, loweralkoxy, diloweralkylamino, nitro or trifluoromethyl;

B is selected from oxygen or sulfur;

R is selected from the group consisting of hydrogen, loweralkyl, cycloalkyl, or phenyl-loweralkyl of which phenyl may be optionally substituted by one or two radicals selected from halo, loweralkyl, loweralkoxy, nitro or trifluoromethyl;

n is 1, 2 or 3;

$R^4$ and $R^5$ are selected from hydrogen or loweralkyl (1-5 C);

Z is selected from the group consisting of $-NR^1R^2$, 1H-pyrazol-1-yl, 1H-imidazol-1-yl, 1H-imidazol-2-yl or 4,5-dihydro-1H-imidazol-2-yl;

$R^1$ and $R^2$ are selected from the group consisting of loweralkyl, cycloalkyl and phenyl-loweralkyl, of which phenyl may be optionally substituted by 1 or 2 radicals selected from halo, loweralkyl, loweralkoxy, nitro, trifluoromethyl or cyano, or $R^1$ and $R^2$ taken together with the adjacent nitrogen atom may form a heterocyclic residue selected from the group consisting of 1-azetidinyl, 1-pyrrolidinyl, 2,5-dimethylpyrrolidin-1-yl, 2-methylpyrrolidin-1-yl, 1-piperidinyl, 4-substituted piperidin-1-yl, 4-[bis(4-fluorophenyl)methyl]-piperidin-1-yl, 4-morpholinyl, 1-piperazinyl, 4-substituted piperazin-1-yl, 1,2,3,6-tetrahydropyridin-1-yl, 2,5-dihydro-1H-pyrrol-1-yl or 1H-pyrrol-1-yl, and the pharmaceutically acceptable acid addition salts thereof. The invention includes individual processes for preparing the novel chemical intermediates of Formulas II and III, respectively.

It is therefore an object of the present invention to provide a novel process for the preparation of aromatic-1,4-oxazepin-ones and thiones of Formula I from haloaromatic carboxylates and alkanolamines.

Another object is to provide novel chemical intermediates useful in the preparation of aromatic-1,4-oxazepin-ones of Formula I and processes for making the intermediates.

Additional objects and advantages of the present invention will become apparent from the following description of the best mode of carrying out the present invention and from the appended claims.

The novel chemical intermediates leading to the preparation of compounds of Formula I have the Formulas II and III as follows:

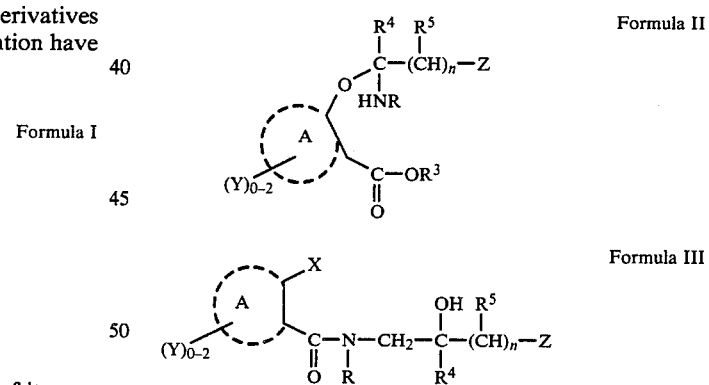

wherein;

A represents an aromatic ring selected from benzene, naphthalene, pyridine or quinoline, any of the rings optionally substituted by one or two radicals selected from halo, loweralkyl, loweralkoxy, nitro, or trifluoromethyl, X is halo and Y, R, $R^4$, $R^5$ and Z are as defined under Formula I above and $R^3$ is selected from hydrogen, alkali-metal ion or an esterifying group, and the acid addition salts thereof.

The novel process involves reaction of an appropriate halo-aromatic-carboxylate and an alkanolamine to give the compounds of Formula II or III and thereafter cyclizing to give compounds of Formula I. The equations involved in the two principal variations of the process are illustrated in Charts I and II, but the invention is not limited thereby.

CHART I
Variation A for Preparing Oxazepinones (and Thiones)

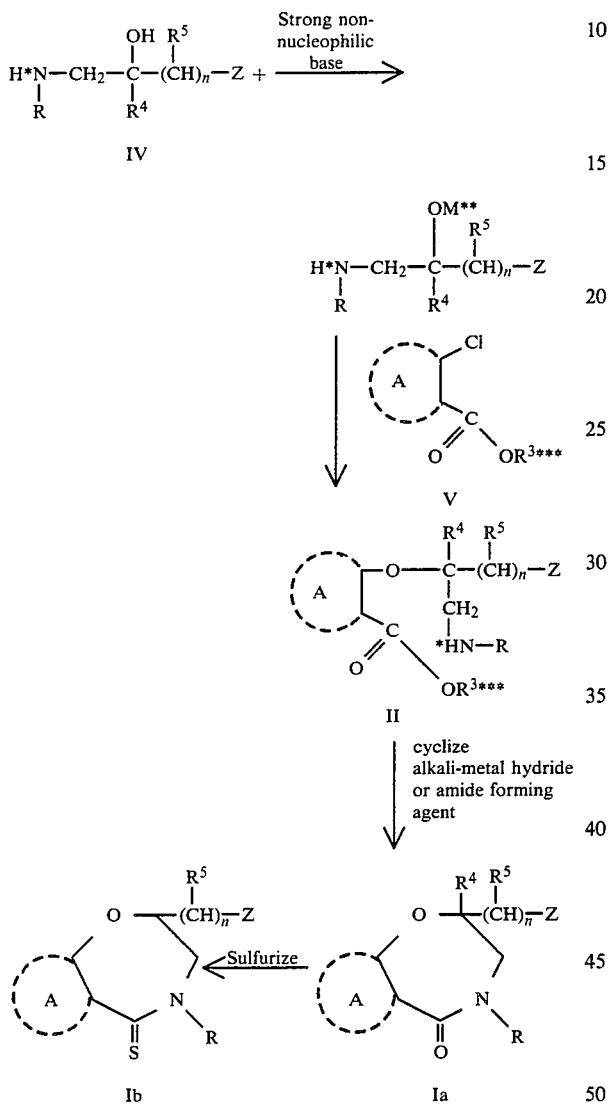

*Amino group may be protected during reaction with base and deprotected afterward. Illustration of preparation of protected aminoalcohol:

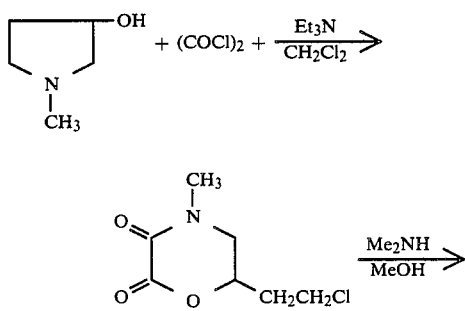

-continued
CHART I
Variation A for Preparing Oxazepinones (and Thiones)

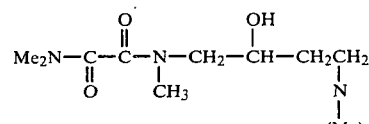

**Alkali-metal ion.
***$R^3$ = esterifying radical, H or alkali-metal.

CHART II
Variation B for Preparing Oxazepinones (and Thiones)

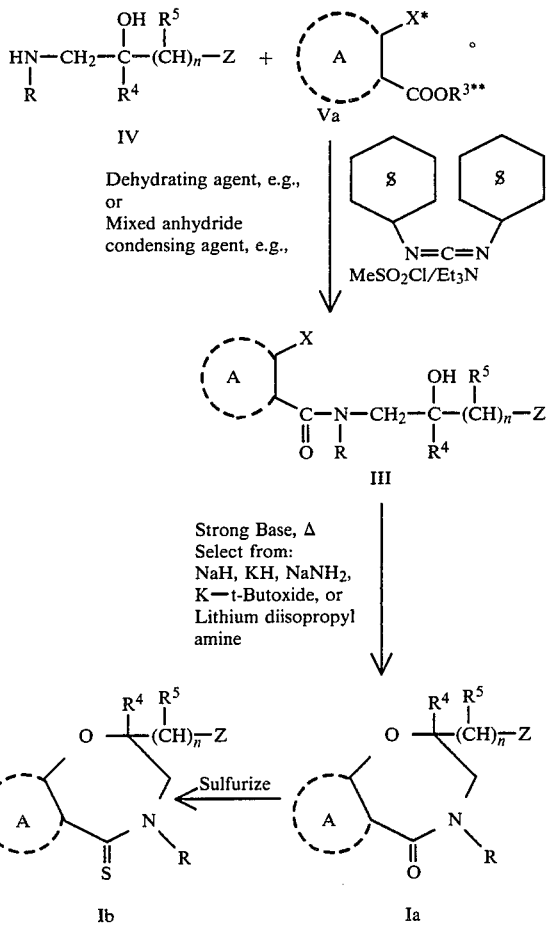

*X = halo.
**$R^3$ = H, alkali-metal.

In the further definition of symbols in the formulas hereof and where they appear elsewhere throughout this specification and the claims, the terms have the following significance.

The term "loweralkyl" as used herein includes straight and branched chain radicals of up to eight carbons inclusive and is exemplified by such groups as methyl, ethyl, propyl, isopropyl, butyl, sec-butyl, tert-butyl, amyl, isoamyl, hexyl, heptyl and octyl radicals and the like. The term "loweralkoxy" has for formula —O-loweralkyl.

The term "cycloalkyl" as used herein includes primarily cyclic alkyl radicals containing 3-9 carbon atoms inclusive and includes such groups as cyclopropyl, cyclobutyl, cyclopentyl, cyclohexyl, methylcyclohexyl, cycloheptyl and the like.

The terms halo and halogen when referred to herein include fluorine, chlorine, bromine and iodine unless otherwise stated.

"Pharmaceutically acceptable salts" include acid addition salts, hydrates, alcoholates and quaternary salts of the compounds of Formula I which are physiologically compatible in warm-blooded animals. The acid addition salts may be formed by either strong or weak acids. Representative of strong acids are hydrochloric, sulfuric and phosphoric acids. Representative of weak acids are fumaric, maleic, succinic, oxalic, citric, tartaric, hexamic and the like.

Suitable quaternary salts include those formed with the loweralkyl halides and loweralkyl sulfates.

By sulfurizing agent is meant any agent or mixture of agents which will convert oxazepinones to oxazepinethiones such as 2,4-bis(4-methoxyphenyl-1,3,2,4-dithiadiphosphetane-2,4-disulfide or a mixture of phosphorus pentasulfide and alkali metal sulfide or phosphorus pentasulfide in pyridine, acetonitrile or other solvents.

The term "protected amine function" refers to the amine function of an alkanolamine which has undergone temporary reaction to eliminate competition with formation of desired alkoxide when the alkanolamine is reacted with a strong non-nucleophilic base.

The term "deprotecting the amine function" refers to the act of regenerating the amine function of the chemical intermediate usually by hydrolysis.

The oxazepinones and oxazepinethione compounds of Formula I exhibit anti-histamine activity in guinea pigs. The method of testing is a modification of the procedure of Tozzi et al (Agents and Actions, Vol. 4/4, 264–270, 1974) as follows. Guinea pigs are fasted 18–24 hr in individual cages. Water is available ad libitum. On the test day, animals in groups of 3 are injected intraperitoneally with 30 mg/kg of the test compound prepared in an appropriate vehicle. Thirty minutes later, histamine at a dosage level of 1.2 mg/kg (=2×the $LD_{99}$) is injected into a marginal ear vein. Survival of the guinea pigs for 24 hrs is positive evidence of antihistamine activity. If the vehicle used for the test compound is other than water, its effect is established by testing an equal amount as a control. The dose protecting 50% of the animals ($PD_{50}$) from death may be established from dose response curves. The compounds have low potential for sedation.

DETAILED DESCRIPTION OF THE INVENTION

The present invention encompasses a novel process for preparing aromatic-1,4-oxazepinones and thiones by reaction of haloaromatic carboxylates an alkanolamines followed by cyclization of the novel chemical intermediates produced therein.

The novel process of the invention comprises the steps of:

Step 1, reacting an aromatic compound of the formula:

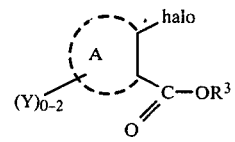

wherein A is as defined under Formulas II and III above, and Y is defined under Formula I, and $R^3$ is selected from hydrogen, an alkali-metal or an esterifying group with an alkanolamine compound of the formula:

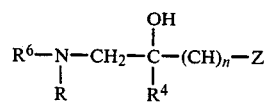

wherein Z, R, $R^4$, $R^5$ and n are as defined under Formula I and $R^6$ is hydrogen or an amine protecting group using one of the following conditions (a) and (b):

(a) firstly, reacting the alkanolamine compound or alkanolamine compound having a protected or unprotected amine function with a strong alkali-metal non-nucleophilic base, and secondly, reacting the product thereof with the aromatic compound and deprotecting the amine function, if protected, to give a compound of the formula:

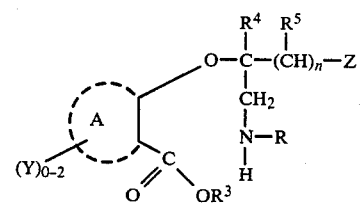

wherein A, Z, Y, R, $R^3$, $R^4$, $R^5$ and n have the starting values, or (b) reacting the aromatic compound wherein $R^3$ is hydrogen or alkali-metal with the alkanolamine in the presence of a dehydrating agent or a condensation agent to give a compound of the formula:

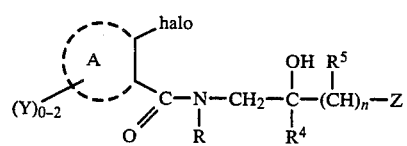

wherein A, Z, Y, R, $R^4$, $R^5$ and n have the starting values;

Step 2, cyclizing a compound prepared in step 1 to give a compound of the formula:

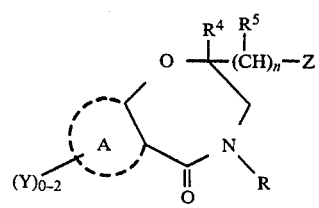

wherein A, Z, Y, R, $R^4$, $R^5$ and n have the starting values and as defined under Formula I, and Step 3, optionally when desired, reacting a compound prepared in step 2 with a sulfurizing agent to give a compound of the formula:

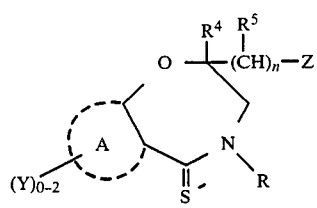

Ib wherein A, Z, Y, R, $R^4$, $R^5$ and n have the starting values and as defined under Formula I.

Compounds of Formula Ia and Ib are encompassed by Formula I.

In reference to the processes of the invention as they apply to the preparation of compounds of Formulas I, II, and III, the following further description is pertinent.

In Step 1, an aromatic halide having a carboxylic acid function in an adjacent position is reacted with an alkanolamine to give either an ether or a carboxamide type intermediate.

In the first variation of Step 1, i.e., Step 1-a, the alkanolamine is reacted with a strong non-nucleophilic base such as potassium hydride, sodium hydride, sodamide or potassium t-butoxide, preferably potassium hydride in an appropriate solvent such as tetrahydrofuran at a suitable temperature. The haloaromatic carboxylic acid or carboxylate is added to the solution, cooling usually being required. When an unprotected alkanolamine is used, potassium hydride is the preferred base. When a protected alkanolamine [i.e., the amine function is prevented from competing for the base (see bottom of Chart I)], any of the strong non-nucleophilic bases are suitable. The protecting group is removed by hydrolysis. The resulting compounds, Formula II, are isolated by conventional means, usually by evaporating and partitioning between water and a suitable solvent such as isopropyl ether, the product potassium carboxylate salt being in the aqueous layer. The product is obtained by evaporation and precipitation or the solution is used in the next step. In the second variation, i.e., Step 1-b, the alkanolamine and haloaromatic carboxylic acid or salt thereof are reacted in the presence of a dehydrating agent, preferably dicyclohexylcarbodiimide (DCC) in a suitable solvent such as acetonitrile and water, or in the presence of a mixed anhydride condensation agent, preferably mesyl chloride in pyridine. The reaction is exothermic and requires cooling. When DCC is used and the alkanolamine is a primary amine, the yield is greatly enhanced by the use of an N-hydroxy compound such as 1-hydroxybenzotriazole. Unreacted dicyclohexylcarbodiimide is decomposed by acidifying and the mixture is filtered and the solid discarded. The mixture is evaporated to remove most of the solvent and the product is isolated by partitioning between a suitable organic solvent, preferably chloroform or methylene chloride and aqueous base, the product being in the organic solvent layer and isolatable therefrom by conventional means such as evaporation and precipitation.

In Step 2, cyclization of the ether type carboxylic acid and ester intermediates (Formula II) prepared in Step 1a may be accomplished by use of additional strong non-nucleophilic base in suitable heated solvent, preferably tetrahydrofuran, see Examples 2 and 6. Example 6 illustrates the total synthesis without isolating the intermediate and using 2 molar equivalents of potassium hydride. Example 7 illustrates the use of cyclizing agent: phenyl-N-phenylphosphoramidochloridate [preparation described by Mestres, R. and Polomo, C. in Synthesis (Apr. 1982), page 288–291] using the ether (Formula II) compound as potassium carboxylate salt. The amide type intermediates (Formula III) prepared in Step 1-b are cyclized using a strong non-nucleophylic base selected from such as alkali-metal hydride, alkali-metal amide or K-t-butoxide in a suitable refluxing solvent such as tetrahydrofuran or toluene. Products are isolated by usual procedures as illustrated in Examples 1 and 3, conveniently as an acid addition salt. The free base of any acid addition salt in the process may be generated by partitioning between a suitable solvent for the free base and an aqueous basic solution.

In Step 3, the compounds of Formula Ia may be converted to the thione of Formula Ib by heating together with a sulfurizing agent in a suitable solvent such as pyridine or toluene, see Examples 4 and 5. The thione may be isolated by conventional means, preferably by partitioning between an organic solvent and dilute alkali-metal base and crystallizing from a suitable solvent as an acid addition salt.

Starting materials for the preparation of compounds of Formula IV are obtained by known procedures 1 and 2 represented by equations in Charts III and IV.

CHART III

Preparation of Starting Alkanolamines,
Procedure 1 - (n = 2 or 3)

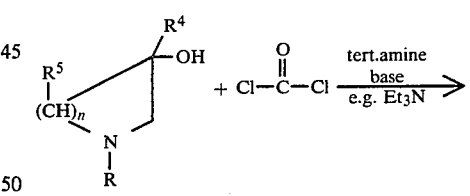

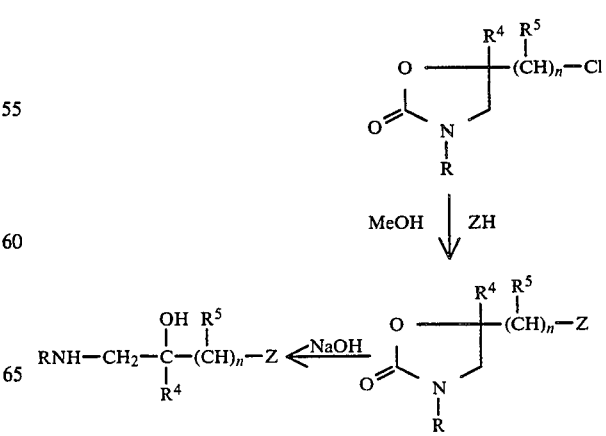

CHART IV
Preparation of Starting Alkanolamines,
Procedure 2 - (n = 1, 2 or 3)

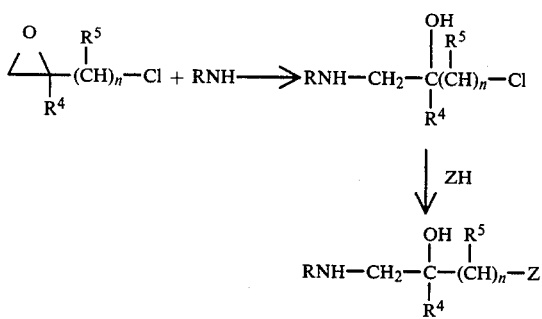

The starting compounds of Formula V are generally available by methods in the literature.

The following preparations and examples illustrate the preparation of chemical intermediates and the aromatic 1,4-oxazepinones and thiones and the process of the invention.

Attached Table 1 illustrates by structure the antihistaminic aromatic-1,4-oxazepinones and thiones of Formula I and not limited to salt form shown, which may be prepared by the process of the invention utilizing an appropriate alkanolamine and appropriate haloaromatic carboxylic acid or carboxylate in the procedures outlined herein; however, the scope of the invention is not limited thereby.

PREPARATION 1

2-Chloro-N-[4-(dimethylamino)-2-hydroxybutyl]-3-pyridinecarboxamide monohydrochloride To a suspension of 11.9 g (0.076 mole) of 2-chloronicotinic in 200 ml of methylene chloride was added 10.2 g (0.076 mole) of 1-hydroxybenzotriazole, 10 g (0.076 mole) of 1-amino-4-(dimethylamino)-2-butanol, and 15.6 g (0.076 mole) of dicyclohexylcarbodiimide. The resulting solution was stirred at room temperature[1] for 6 hrs and allowed to stand for 66 hrs. The resulting mixture was filtered and the filtrate concentrated on the rotary evaporator. The residue was shaken with a mixture of dilute hydrochloric acid and isopropyl ether. The resulting 3 phase system (1 solid, 2 liquid) was filtered and the solid discarded. The aqueous layer was separated, made basic with sodium hydroxide and extracted 3 times with chloroform. The chloroform extracts were combined, dried over anhydrous sodium sulfate and concentrated. The residue was dissolved in isopropyl alcohol and acidified with ethereal hydrogen chloride. The resulting precipitate was dissolved by heating and adding methanol. The crystals obtained on cooling were recrystallized from ethanol. Yield of title compound was 9.6 g (41%), m.p. 182°–192° C.

[1] The procedure was repeated, an exothermic condition requiring cooling being observed, and an increased yield of product of 78% of theory was obtained.

Analysis: Calculated for $C_{12}H_{19}N_3O_2Cl_2$: C,46.77; H,6.21; N,13.63 Found: C,46.67; H,6.42; N,13.91

PREPARATION 2

2-Chloro-N-[3-(dimethylamino)-2-hydroxypropyl]-N-methyl-3-pyridinecarboxamide

To a stirred mixture of 24.1 g (0.143 mole) of 1-dimethylamino-3-methylamino-2-propanol, 22.6 g (0.143 mole) of 2-chloronicotinic acid, 150 ml of acetonitrile and 60 ml of water (2 layer system) was added a solution of 33 g (0.16 mole) of dicyclohexylcarbodiimide in 90 ml of acetonitrile in four portions. After addition of the second portion, an ice bath was necessary for controlling the temperature to around 25° C. After the addition was complete, the mixture was allowed to stand for 2.5 hr, and 10 g of 2-chloronicotinic acid was added to the reaction mixture. The mixture was allowed to stand for 1 hr and a solution of 15 g of dicyclohexylcarbodiimide in 200 ml of acetonitrile was added. The reaction mixture was stirred overnight at room temperature. Concentrated hydrochloric acid was added to bring the reaction mixture to pH of 2 in order to convert the excess carbodiimide to urea. The resulting white solid was removed by filtration and rinsed with aqueous acetonitrile. The filtrate and washings were evaporated to a paste which was partitioned between methylene chloride and potassium carbonate solution. The aqueous layer was extracted two more times with methylene chloride. The methylene chloride solutions were back washed with sodium chloride solution, dried over anhydrous sodium sulfate and evaporated to give 56 g of oil. This oil was chromatographed on 250 g of silica gel eluting with methanol to give 26.97 g of light brown oil containing mainly the title compound.

PREPARATION 3A TO C

Following the procedure of Preparation 2 but substituting the following for 1-dimethylamino-3-methylamino-2-propanol:
4-dimethylamino-1-methylamino-2-butanol,
4-diethylamino-1-methylamino-2-butanol, and
4-(pyrrolidin-1-yl)-methylamino-2-butanol there are obtained:

3(a) 2-chloro-N-[4-(dimethylamino)-2-hydroxybutyl]-N-methyl-3-pyridinecarboxamide, 3(b) 2-chloro-N-[4-(diethylamino)-2-hydroxybutyl]-N-methyl-3-pyridinecarboxamide, and 3(c) 2-chloro-N-[4-(pyrrolidin-1-yl)-2-hydroxybutyl]-N-methyl-3-pyridinecarboxamide.

PREPARATION 4

2-[2-(1-Amino-4-dimethylamino-2-butyloxy)]-3-pyridinecarboxylic acid potassium salt To a solution of 13.2 g (0.1 mole) of 1-amino-4-(dimethylamino)-2-butanol in 50 ml of dry tetrahydrofuran was added, dropwise with stirring, a solution of 25 g (0.22 mole) of 35% potassium hydride in 75 ml of tetrahydrofuran. After the mixture was stirred for 10 min, 15.7 g (0.1 mole) of 2-chloro-3-pyridinecarboxylic acid was added in about 1 g portions over a 10 minute period, cooling at about half way through the addition to bring the temperature down from 60° C. to about room temperature. After the mixture had stirred overnight, it was concentrated on a rotary evaporator under reduced pressure. The residue was partitioned between water and isopropyl ether. The water layer was concentrated on a rotary evaporator under reduced pressure to give the title product.

PREPARATION 5

2-[2-(1-Methylamino-4-dimethylamino-2-butyloxy)]-3-pyridinecarboxylic acid potassium salt Following the procedure of Preparation 4, but substituting 4-(dimethylamino)-1-methylamino-2-butanol for 1-amino-4-dimethylamino-2-butanol, the title compound is obtained.

PREPARATION 6A AND B

Following the procedure of Preparation 4 but substituting for 4-(dimethylamino)-1-methylamino-2-butanol, 1-methylamino-4-(diethylamino)-2-butanol, and 1-methylamino-4-(pyrrolidin-1-yl)-2-butanol there are obtained:

(a) 2-[2-(1-methylamino-4-diethylamino-2-butyloxy)]-3-pyridinecarboxylic acid potassium salt, and (b) 2-[2-(1-methylamino-4-(pyrrolidin-1-yl-2-butoxy)]-3-pyridinecarboxylic acid potassium salt.

EXAMPLE 1

2-[(Dimethylamino)methyl]-2,3-dihydro-4-methylpyrido[3,2-f][1,4]oxazepin-5(4H)-one fumarate [1:1]

A solution of 26.97 g (0.099 mole) of 2-chloro-N-[3-(dimethylamino)-2-hydroxypropyl]-N-methyl-3-pyridinecarboxamide obtained in Preparation 2 in 200 ml of toluene was heated to remove about 40 ml of distillate and thereafter refluxed under a Dean-Stark trap for 0.5 hr. Sodium hydride (50% suspension in mineral oil), 15 g (0.3 mole) was added portionwise to the solution at room temperature. The mixture was then heated to reflux for 20 min. Isopropanol and celite were added and the resulting mixture was filtered. The filtrate was acidified with a hydrogen chloride solution in isopropyl alcohol. White precipitate was collected by filtration, rinsed with isopropyl alcohol-isopropyl ether mix and dried under a nitrogen atmosphere to protect against moisture pickup. Weight of this first crop was 11 g. Second and third crystal crops were obtained. All three crops were combined and dissolved in water. The solution was made basic with excess potassium carbonate and extracted three times with methylene chloride. The methylene chloride solutions were back washed with saturated sodium chloride solution, dried over magnesium sulfate, treated with activated charcoal, filtered and evaporated to give 8.8 g of brown oil. A 1.9 g sample of the brown oil was dissolved in methanol and kept warm on a steam bath. Fumaric acid, 0.94 g, was added and the solution concentrated to a small volume. Acetone was added to precipitate the fumarate salt which was then recrystallized using methanol and acetone to give 1.4 g of white solid, m.p. 150°–151° C.

Analysis of the recrystallized solid was as follows: Calculated for $C_{16}H_{21}N_3O_6$: C,54.70; H,6.02; N,11.96 Found: C,54.69; H,6.07; N,11.88.

EXAMPLE 2

2-[2-(Dimethylamino)ethyl]-2,3-dihydro-4-methyl-1,4-oxazepino[6,7-c]quinolin-5(4H)-one oxalate [1:1]

A solution of 30 g (0.21 mole) of 4-dimethylamino-1-methylamino-2-butanol in 50 ml of tetrahydrofuran was added dropwise to a suspension of 29 g (0.25 mole) of 35% potassium hydride in mineral oil in 100 ml of tetrahydrofuran at room temperature. The resulting turbid solution was added slowly (15 min) to a stirred suspension of 50 g (0.21 mole) of 3-carboxyethyl-4-chloroquinoline in 400 ml of tetrahydrofuran. The mixture was stirred overnight and filtered. The filtrate was concentrated and the residue was partitioned between dilute hydrochloric acid and chloroform. The acid layer was extracted twice more with chloroform. The acid layer was made basic with sodium hydroxide and extracted three times with chloroform. The last three chloroform extracts were dried over anhydrous sodium sulfate and concentrated. The residue was dissolved in 200 ml of tetrahydrofuran and 3.4 g of 60% sodium hydride in mineral oil was added. The mixture was heated to reflux for 15 hr, cooled and treated with water. The mixture was partitioned between chloroform and dilute hydrochloric acid. The acid layer was made basic with sodium hydroxide and extracted with chloroform. The chloroform layer was concentrated and the residue was chromatographed on HPLC, using a silica gel column and eluting with 97% ethanol-3% triethylamine. The yield of product, the free base of the title compound on evaporation of solvent was 6 g (10%). A 1.5 g sample of the free base was treated with 0.5 g of oxalic acid in 10 ml of ethanol. The resulting crystals weighed 2 g, m.p. 214°–218° C.

Analysis: Calculated for $C_{19}H_{23}N_3O_6$: C,58.60; H,5.95; N,10.79 Found: C,58.46; H,6.10; N,10.75.

EXAMPLE 3

2-[2-(Dimethylamino)ethyl]-2,3-dihydropyrido[3,2-f]-1,4-oxazepin-5(4H)-one fumarate [1:1]

Eight grams (0,026 mole) of the hydrochloride salt of 2-chloro-N-[4-(dimethylamino)-2-hydroxybutyl]-3-pyridinecarboxamide obtained in Preparation 1 was converted to the free base by partitioning between chloroform and dilute sodium hydroxide. The chloroform layer containing the free base was dried over sodium sulfate and concentrated to give a residue which was dissolved in 80 ml of dry benzene and further dried by distilling off the benzene. The residue, the dry free base, was dissolved in 20 ml of dry tetrahydrofuran. This solution was added to a stirred suspension of 8.3 g (0.052 mol) of potassium hydride (35% in mineral oil) in 80 ml dry tetrahydrofuran. The mixture was stirred at reflux for 4 hr and cooled. Ten ml of isopropyl alcohol was added. The solution was partitioned between isopropyl ether and dilute hydrochloric acid. The acid layer was made basic with sodium hydroxide and extracted four times with chloroform. The combined chloroform extract was concentrated and the residue chromatographed on HPLC (silica gel; 90% ethanol-10% triethylamine). The fractions containing the free base of the title compound were concentrated. The residue, the free base, 1.3 g, was reacted with 0.7 g of fumaric acid in 25 ml of isopropyl alcohol to give 1.2 g (13%) of the fumarate salt, m.p. 160°–164° C.

Analysis: Calculated for $C_{16}H_{21}N_3O_6$: C,54.69; H,6.02; N,11.96 Found: C,54.29; H,6.02 N,11.54.

EXAMPLE 4

2-[2-(Dimethylamino)ethyl]-2,3-dihydropyrido[3,2-f]-1,4-oxazepine-5(4H)-thione dihydrochloride monohydrate To a solution of 5 g (0.021 mole) of 2-[2-(dimethylamino)ethyl]-2,3-dihydropyrido[3,2-f][1,4]-oxazepin-5(4H)-one in 50 ml of pyridine was added 5.1 g (0.023 mole) of phosphorus pentasulfide. The reaction was exothermic. When the temperature had dropped, the mixture was heated to 70° C. for 3.5 hr. The mixture was allowed to cool and it was then partitioned between dilute sodium hydroxide solution and chloroform while cooling by addition of ice. The aqueous layer was extracted three more times with chloroform. The combined chloroform extracts were dried over anhydrous sodium sulfate and concentrated. The residue was dissolved in 40 ml of ethanol and acidified with ethereal hydrogen chloride. The crystalline salt obtained was recrystallized from 95% ethanol to give 1.4 g (19%), m.p. 172°–175° C.

Analysis: Calculated for $C_{12}H_{21}N_3SO_2Cl_2$: C,42.10; H,6.18; N,12.28 Found: C,42.66; H,5.74; N,12.34.

EXAMPLE 5

2-[(Dimethylamino)methyl]-2,3-dihydro-4-methylpyrido[3,2-f][1,4]oxazepine-5(4H)-thione hemifumarate To a solution of 4.8 g of 2-[(dimethylamino)methyl]2,3-dihydro-4-methylpyrido[3,2-f][1,4]oxazepin-5(4H)-one in 50 ml of toluene was added 4.9 g of 2,4-bis(4-methoxyphenyl)-1,3,2,4-dithiadiphosphetane-2,4-disulfide. The reaction mixture was kept at reflux for two hours. Concentrated potassium carbonate solution was added which caused separation to give a three-layer system: a toluene layer, an aqueous layer and a gummy layer. Only the toluene and aqueous layer contained the desired free base of the title compound. The layers were separated and the gummy layer was discarded. The aqueous layer was extracted three times with methylene chloride. The methylene chloride extracts after washing with saturated sodium chloride solution were combined with the toluene layer. This organic solution was dried over anhydrous sodium sulfate and evaporated to give 5.25 g of oil. The oil, the free base of the title compound, was dissolved in methanol to which solution was added 2.45 g of fumaric acid. The mixture was heated with stirring and isopropyl alcohol was added to the point of cloudiness and the mixture was stirred overnight. Yellow powder was obtained, 2.85 g, which was recrystallized from methanol, m.p. 178°–179° C.

Analysis: Calculated for $C_{14}H_{19}N_3O_3S$: C,54.35; H,6.19; N,13.58; Found: C,54.21; H,6.20; N,13.53.

EXAMPLE 6

2-[2-(Dimethylamino)ethyl]-2,3-dihydro-4-methyl-1,4-oxazepino[6,7-c]quinolin-5(4H)-one To a suspension of 19.4 g (35% in oil, 0.172 mole) of potassium hydride in 150 ml of tetrahydrofuran was added at a rapid drop, 12.4 g (0.086 mole) of 4-dimethylamino-1-methylamino-2-butanol. After 10 min., 20 g (0.086 mole) of 3-carboxyethyl-4-chloroquinoline was added via a powder dropping funnel over a period of 30 min. The mixture was stirred at room temperature overnight. Approximately 50 ml of water was added to quench the reaction and the mixture was partitioned between isopropanol ether and water. The aqueous layer was extracted again with two 70 ml portions of isopropyl ether. The aqueous layer was then continuously extracted for 15 hr with chloroform. The chloroform layer was collected, filtered and concentrated by rotary evaporation at 80°, 30 mm. The crude material (18 g) was purified by HPLC using silica gel as the stationary phase and 3% triethylamine/ethanol as the eluent. Approximately 4 g (b 15.6%) of product was obtained on evaporation of fractions having a similar thin layer chromatograph (TLC) using ethyl acetate, methanol and aqueous conc. ammonia (7:2:1 parts by volume respectively) on silica. TLC of the final product using the same solvent mix on silica was identical to that of the free base of the same compound prepared in Example 2. C.I. mass spec showed M+H of 300. The oxalate salt was also identical to that obtained in Example 2.

EXAMPLE 7

2-[2-(Dimethylamino)ethyl]-2,3-dihydropyrido[3,2-f]1,4-oxazepin-5(4H)-one

To a solution of 0.01 mole of 2-[2-(1-amino-4-dimethylamino-2-butyloxy)]-3-pyridinecarboxylic acid potassium salt, obtained in Preparation 4 in 40 ml of methylene chloride was added 0.012 mole of triethylamine and 0.02 mole of phenyl-N-phenylphosphoramidochloridate and the solution was stirred overnight at room temperature. The resulting solution was extracted with dilute hydrochloric acid. The acid layer was separated, made basic with sodium hydroxide and extracted continuously for 24 hr with chloroform. The extract was evaporated to give the title product which was shown by NMR to be that of the free base as compared to a known sample.

TABLE 1

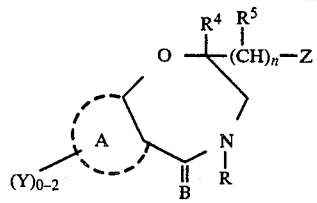

| A(Y)$_{0-2}$ | B | R | R$^4$ | Z | $\underset{-(CH)_n-}{R^5}$ | Salt |
|---|---|---|---|---|---|---|
| benz | O | —CH$_3$ | H | —N(CH$_3$)$_2$ | —(CH$_2$)$_2$— | HCl |
| benz | O | —CH$_3$ | H | —N(CH$_3$)$_2$ | " | — |
| benz | O | —CH$_3$ | H | —N⟨O⟩ | " | fumarate |
| benz | O | —CH$_2$φ | H | —N⟨O⟩ | " | — |
| benz | S | —CH$_3$ | H | —N(CH$_3$)$_2$ | " | HCl |

TABLE 1-continued

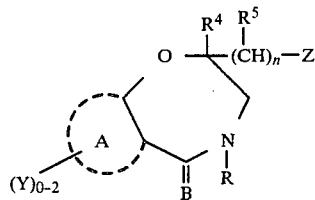

| A(Y)₀₋₂ | B | R | R⁴ | Z | $-\overset{R^5}{\underset{\|}{(CH)_n}}-$ | Salt |
|---|---|---|---|---|---|---|
| benz | O | —CH₂φ | H | —N(CH₃)₂ | " | H₂O |
| benz | S | —CH₃ | H | -N⟨  ⟩O (morpholino) | " | HCl |
| naphth[2,3-f] | O | —CH₃ | H | —N(CH₃)₂ | " | oxalate |
| pyrido[3,2-f] | O | —CH₃ | H | —N(CH₃)₂ | " | 1.5 fumarate |
| pyrido[3,2-f] | S | —CH₃ | H | —N(CH₃)₂ | " | fumarate 0.5 ethanol |
| pyrido[3,2-f] | S | —CH₃ | H | —N(CH₃)₂ | " | fumarate |
| benz | S | —CH₂φ | H | -N⟨  ⟩O (morpholino) | " | — |
| benz | S | —CH₃ | H | -N⟨  ⟩(φ)(OH) (4-phenyl-4-hydroxypiperidino) | " | — |
| benz | S | —CH₃ | H | -N⟨  ⟩=φ (4-phenyl-tetrahydropyridino) | " | — |
| 8-Cl—benz | S | —CH₃ | H | —N(CH₃)₂ | " | HCl |
| 8-Cl—benz | O | —CH₃ | H | —N(CH₃)₂ | " | oxalate |
| 7-Br—benz | O | —CH₃ | H | —N(CH₃)₂ | " | oxalate |
| naph[2,1-f] | O | —CH₃ | H | —N(CH₃)₂ | " | oxalate |
| pyrido[4,3,-f] | O | —CH₃ | H | —N(CH₃)₂ | " | fumarate |
| pyrido[3,4-f] | O | —CH₃ | H | —N(CH₃)₂ | " | fumarate |
| pyrido[2,3-f] | O | —CH₃ | H | —N(CH₃)₂ | " | fumarate |
| pyrido[4,3-f] | S | —CH₃ | H | —N(CH₃)₂ | " | 1.5 HCl |
| pyrido[3,2-f] | S | —CH₃ | H | —N(C₂H₅)₂ | " | — |
| naphth[2,3-f] | S | —CH₃ | H | —N(CH₃)₂ | " | oxalate, ½ H₂O |
| 7,9 diiodobenz | O | —CH₃ | H | —N(CH₃)₂ | " | — |
| 7-Cl—benz | O | —CH₃ | H | —N(CH₃)₂ | " | oxalate |
| pyrido[3,2-f] | O | —CH₃ | H | —N(CH₃)₂ | —CH₂— | — |
| pyrido[3,2-f] | S | —CH₃ | H | —N(CH₃)₂ | —(CH₂)₂— | methiodide |
| 7-Cl—benz | S | —CH₃ | H | —N(CH₃)₂ | " | oxalate.½ H₂O |
| naphth[2,1-f] | S | —CH₃ | H | —N(CH₃)₂ | " | HCl |
| pyrido[3,4-f] | S | —CH₃ | H | —N(CH₃)₂ | " | fumarate |
| pyrido[2,3-f] | S | —CH₃ | H | —N(CH₃)₂ | " | fumarate |
| 7-OCH₃—benz | O | —CH₃ | H | —N(CH₃)₂ | " | oxalate ½ H₂O |
| 7-Br—benz | S | —CH₃ | H | —N(CH₃)₂ | " | oxalate.H₂O |
| benz | O | —C₆H₁₁ | H | —N(CH₃)₂ | " | oxalate |
| benz | O | —C₂H₅ | H | —N(CH₃)₂ | " | oxalate |
| benz | O | —CH(CH₃)₂ | H | —N(CH₃)₂ | " | oxalate |
| benz | O | 4-Cl—C₆H₄CH₂— | H | —N(CH₃)₂ | " | oxalate |
| benz | O | 4-CH₃—C₆H₄CH₂— | H | —N(CH₃)₂ | " | oxalate |
| benz | O | 3,5-(OCH₃)₂—C₆H₃CH₂— | H | —N(CH₃)₂ | " | oxalate |
| benz | O | 3-CF₃—C₆H₄CH₂— | H | —N(CH₃)₂ | " | oxalate |
| benz | O | 4-NO₂—C₆H₄CH₂— | H | —N(CH₃)₂ | " | oxalate |
| pyrido[3,2-b] | O | —C₆H₁₁ | H | —N(CH₃)₂ | " | fumarate |
| pyrido[3,2-f] | O | —C₂H₅ | H | —N(CH₃)₂ | " | fumarate |
| pyrido[3,2-f] | O | —CH(CH₃)₂ | H | —N(CH₃)₂ | " | fumarate |
| pyrido[3,2-f] | O | 4-Cl—C₆H₄CH₂— | H | —N(CH₃)₂ | " | fumarate |
| pyrido[3,2-f] | O | 4-CH₃—C₆H₄CH₂— | H | —N(CH₃)₂ | " | fumarate |
| pyrido[3,2-f] | O | 4-OCH₃—C₆H₄CH₂— | H | —N(CH₃)₂ | " | fumarate |

TABLE 1-continued

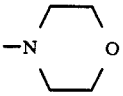

| A(Y)$_{0-2}$ | B | R | R$^4$ | Z | R$^5$<br>\|<br>—(CH)$_n$— | Salt |
|---|---|---|---|---|---|---|
| pyrido[3,2-f] | O | 3-CF$_3$—C$_6$H$_4$CH$_2$— | H | —N(CH$_3$)$_2$ | " | fumarate |
| pyrido[3,2-f] | O | 4-NO$_2$—C$_6$H$_4$CH$_2$— | H | —N(CH$_3$)$_2$ | " | fumarate |
| benz | O | —CH$_3$ | H | 1-pyrrolidinyl | " | fumarate |
| benz | O | —CH$_3$ | H | 1-piperidinyl | " | fumarate |
| benz | O | —CH$_3$ | H | 1-piperazinyl | " | fumarate |
| benz | O | —CH$_3$ | H | 4-CH$_3$—piperizinyl | " | fumarate |
| pyrido[3,4-f] | O | —CH$_3$ | H | —N(CH$_3$)$_2$ | " | ½ H$_2$O<br>2 oxalate |
| pyrido[3,4-f] | S | —CH$_3$ | H | —N(CH$_3$)$_2$ | " | 2 oxalate |
| pyrido[3,2-f] | O | —CH$_3$ | H | 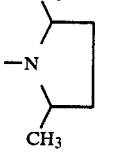 | " | oxalate<br>maleate |
| pyrido[3,2-f] | O | —CH$_3$ | H | 1-pyrrolidinyl | " | 2 fumarate |
| pyrido[3,2-f] | O | —CH$_3$ | H | —N(n-butyl)$_2$ | " | maleate |
| pyrido[3,2-f] | O | —CH$_3$ | H | —N(C$_2$H$_5$)$_2$ | " | oxalate |
| pyrido[3,2-f] | O | —CH$_3$ | H | 1-piperidinyl | " | oxalate |
| pyrido[3,2-f] | O | —CH$_3$ | H | —N(CH$_3$)(benzyl) | " | maleate |
| pyrido[3,2-f] | O | —CH$_3$ | H | —N(CH$_3$)—C$_6$H$_5$ | " | — |
| pyrido[3,2-f] | O | —CH$_3$ | H | 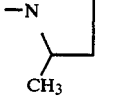 | " | fumarate |
| pyrido[3,2-f] | O | —CH$_3$ | H | 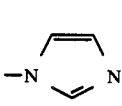 | " | — |
| pyrido[3,2-f] | O | —CH$_3$ | H | 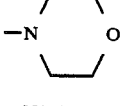 | " | — |
| pyrido[3,2-f] | O | —CH$_3$ | H | 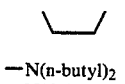 | " | — |
| pyrido[3,2-f] | O | —C$_2$H$_5$ | H | —N(CH$_3$)$_2$ | " | oxalate |
| pyrido[3,2-f] | O | —C$_2$H$_5$ | H | 1-pyrrolidinyl | " | oxalate |
| pyrido[3,2-f] | S | —CH$_3$ | H | 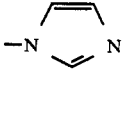 | " | — |
| pyrido[3,2-f] | S | —CH$_3$ | H | —N(n-butyl)$_2$ | " | oxalate |
| pyrido[3,2-f] | S | —CH$_3$ | H | —N(C$_2$H$_5$)$_2$ | " | oxalate |
| pyrido[3,2-f] | S | —CH$_3$ | H | 1-pyrrolidinyl | " | oxalate |
| pyrido[3,2-f] | S | —CH$_3$ | H |  | " | 1.5 oxalate |

TABLE 1-continued

| A(Y)$_{0-2}$ | B | R | R$^4$ | Z | $-\underset{R^5}{(CH)}_n-$ | Salt |
|---|---|---|---|---|---|---|
| pyrido[3,2-f] | S | —C$_2$H$_5$ | H | —N(CH$_3$)$_2$ | " | — |
| pyrido[3,2-f] | S | —CH$_3$ | H | —N(CH$_3$)(benzyl) | " | oxalate |
| 7-Cl—pyrido[3,2-f] | O | —CH$_3$ | H | 1-pyrrolidinyl | " | 2.5 fumarate |
| 7-Cl—pyrido[3,2-f] | O | —CH$_3$ | H | —N(CH$_3$)$_2$ | " | oxalate |
| pyrido[3,2-f] | O | —C$_6$H$_{11}$ | H | —N(CH$_3$)$_2$ | —CH$_2$— | oxalate |
| pyrido[3,2-f] | O | —CH$_2$C$_6$H$_5$ | H | —N(CH$_3$)$_2$ | —(CH$_2$)$_2$— | 1.5 oxalate, ½ H$_2$O |
| pyrido[3,2-f] | O | H | H | —N(CH$_3$)$_2$ | " | — |
| pyrido[3,2-f] | O | H | H | —N(CH$_3$)$_2$ | " | fumarate |
| pyrido[3,2-f] | O | —CH$_3$ | H | —N(CH$_2$)$_2$ | —(CH$_2$)$_3$— | 1.5 fumarate, 0.5 H$_2$O |
| pyrido[3,2-f] | S | —CH$_3$ | H | —N(CH$_3$)$_2$ | " | 2 oxalate |
| 7-Cl—pyrido[3,2-f] | S | —CH$_3$ | H | —N(CH$_3$)$_2$ | —(CH$_2$)$_2$— | ½ H$_2$O, ½ (CH$_3$)$_2$ HOH |
| pyrido[3,2-f] | S | —CH$_3$ | H | —N(CH$_2$C$_6$H$_5$)$_2$ | " | fumarate |
| pyrido[3,2-f] | O | —CH$_3$ | H | 4-methyl-piperazin-1-yl | " | 2.0 fumarate, hydrate |
| pyrido[3,2-f] | S | —CH$_3$ | H | 4-methyl-piperazin-1-yl | " | 2.0 fumarate, ½ H$_2$O |
| pyrido[3,2-f] | O | —CH$_3$ | H | —N(CH$_2$—4F—C$_6$H$_4$)$_2$ | " | 2.0 fumarate, ½ H$_2$O |
| pyrido[3,2-f] | S | —CH$_3$ | H | —N(CH$_3$)(C$_6$H$_5$) | " | — |
| pyrido[3,2-f] | S | H | H | —N(CH$_3$)$_2$ | " | 2 HCl, H$_2$O |
| pyrido[3,2-f] | S | —CH$_3$ | H | —N(CH$_2$—4F—C$_6$H$_4$)$_2$ | " | oxalate, H$_2$O |
| pyrido[3,2-f] | S | —CH$_3$ | H | 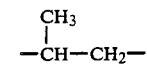 | " | — |
| pyrido[3,2-f] | O | —CH$_3$ | H | —N(CH$_3$)$_2$ | $-\underset{\underset{CH_3}{\|}}{CH}-CH_2-$ | oxalate |
| pyrido[3,2-f] | O | —CH$_3$ | —CH$_3$ | —N(CH$_3$)$_2$ | " | 2 HCl |
| pyrido[3,2-f] | S | —CH$_3$ | —CH$_3$ | —N(CH$_3$)$_2$ | " | HCl |
| 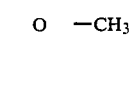 | O | —CH$_3$ | H | —N(CH$_3$)$_2$ | " | oxalate |
| pyrido[3,2-f] | S | —CH$_3$ | H | —N(CH$_3$)$_2$ | " | oxalate |
| pyrido[3,2-f] | O | —CH$_3$ | H | —N(CH$_3$)$_2$ | $-CH_2-\underset{\underset{}{\overset{CH_3}{\|}}}{C}-$ | HCl |
| pyrido[3,2-f] | S | —CH$_3$ | H | 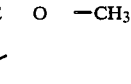 | —(CH$_2$)$_2$— | { fumarate, isopropyl alcohol |
| 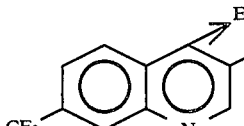 | O | —CH$_3$ | H | —N(CH$_3$)$_2$ | " | fumarate |

TABLE 1-continued

| A(Y)₀₋₂ | B | R | R⁴ | Z | $-(CH)_n-$ with R⁵ | Salt |
|---|---|---|---|---|---|---|
|  | O | —CH₃ | H | —N(CH₃)₂ | " | fumarate, 0.5 H₂O |
| 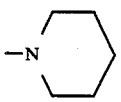 | S | —CH₃ | H | —N(CH₃)₂ | " | fumarate, isopropyl alcohol, H₂O |
| pyrido[3,2-f] | S | —CH₃ | H | 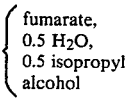 | " | fumarate, 0.5 H₂O, 0.5 isopropyl alcohol |
| 6-Cl—pyrido[4,3-f] | S | —CH₃ | H | —N(CH₃)₂ | " | 0.5 fumarate |
| 6-[N(CH₃)₂]—pyrido[4,3-f] | O | —CH₃ | H | —N(CH₃)₂ | " | 1.5 fumarate |
| pyrido[3,2-f] | O | —CH₃ | H |  | " | 2.0 fumarate |
| pyrido[3,2-f] | S | —CH₃ | H |  | " | fumarate |
| pyrido[3,2-f] | O | —CH₃ | H |  | " | oxalate, 0.5 H₂O |
| pyrido[3,2-f] | O | —CH₃ | H | —N(CH₃)₂ | —CH₂— | fumarate |
| pyrido[3,2-f] | S | —CH₃ | H | —N(CH₃)₂ | " | 0.5 fumarate |
| pyrido[3,2-f] | O | —CH₃ | H | —N(CH₃)₂ | —(CH₂)₂ | — |
| 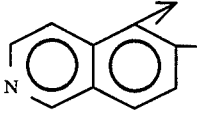 | O | —CH₃ | H | —N(CH₃)₂ | —(CH₂)₂— | oxalate |
| 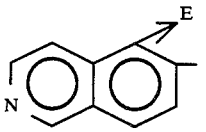 | S | —CH₃ | H | —N(CH₃)₂ | " | HCl |
| 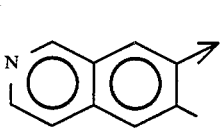 | O | —CH₃ | H | —N(CH₃)₂ | " | oxalate |

TABLE 1-continued
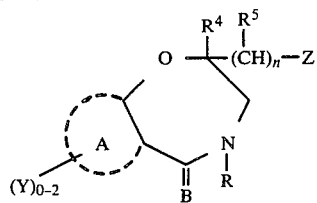
| A(Y)₀₋₂ | B | R | R⁴ | Z | —(CH)ₙ— (R⁵) | Salt |
|---|---|---|---|---|---|---|
| quinoline-N (6-E, 3-CH₃) | S | —CH₃ | H | —N(CH₃)₂ | " | HCl |
| quinoline-N (8-E, 4-CH₃) | O | —CH₃ | H | —N(CH₃)₂ | " | oxalate |
| quinoline-N (8-E, 4-CH₃) | S | —CH₃ | H | —N(CH₃)₂ | " | HCl |
| quinoline (3-CH₃, 8-E) | O | —CH₃ | H | —N(CH₃)₂ | " | oxalate |
| quinoline (3-CH₃, 8-E) | S | —CH₃ | H | —N(CH₃)₂ | " | HCl |
| quinoline (6-E) | O | —CH₃ | H | —N(CH₃)₂ | " | oxalate |
| quinoline (6-E) | S | —CH₃ | H | —N(CH₃)₂ | " | HCl |
| quinoline (3-E) | O | —CH₃ | H | —N(CH₃)₂ | " | oxalate |
| quinoline (3-E) | S | —CH₃ | H | —N(CH₃)₂ | " | HCl |

What is claimed is:

1. A process for the preparation of a compound of the formula:

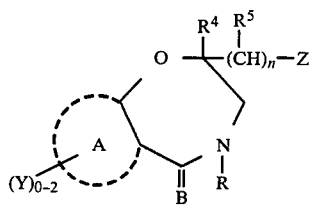

wherein:
- A represents an aromatic ring having two of its carbon atoms held mutually with the oxazepine moiety selected from the group consisting of benzene, naphthalene, quinoline or pyridine, any of the rings optionally substituted by one or two Y radicals selected from the group consisting of halo, loweralkyl, loweralkoxy, diloweralkylamino, nitro or trifluoromethyl;
- B is selected from oxygen or sulfur;
- R is selected from the group consisting of hydrogen, loweralkyl, cycloalkyl or phenylloweralkyl of which phenyl may be optionally substituted by one or two radicals selected from halo, loweralkyl, loweralkoxy, nitro or trifluoromethyl;
- n is 1, 2 or 3;
- $R^4$ and $R^5$ are selected from hydrogen or loweralkyl (1–5 C);
- Z is selected from the group consisting of $-NR^1R^2$, 1H-pyrazol-1-yl, 1H-imidazol-1-yl, 1H-imidazol-2-yl or 4,5-dihydro-1H-imidazol-2-yl;
- $R^1$ and $R^2$ are selected from the group consisting of loweralkyl, cycloalkyl and phenyl-loweralkyl of which phenyl may be optionally substituted by 1 or 2 radicals selected from halo, loweralkyl, loweralkoxy, nitro, trifluoromethyl or cyano, or $R^1$ and $R^2$ taken together with the adjacent nitrogen atom may form a heterocyclic residue selected from the group consisting of 1-azetidinyl, 1-pyrrolidinyl, 2,5-dimethylpyrrolidin-1-yl, 2-methylpyrrolidin-1-yl, 1-piperidinyl, 4-substituted piperidin-1-yl, 4-[bis(4-fluorophenyl)methyl]-piperidin-1-yl, 4-morpholinyl, 1-piperazinyl, 4-substituted-piperazin-1-yl, 1,2,3,6-tetrahydropyridin-1-yl, 2,5-dihydro-1H-pyrrolo-1-yl, or 1H-pyrrol-1-yl, and the pharmaceutically acceptable acid addition salts thereof, which comprises the steps of (Step 1) reacting an aromatic compound of the formula:

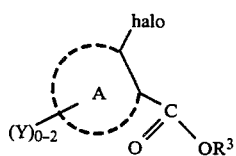

where A represents an aromatic ring selected from benzene, naphthalene, pyridine or quinoline, any of the rings optionally substituted by one or two radicals selected from halo, loweralkyl, loweralkoxy, diloweralkylamino, nitro or trifluoromethyl, and $R^3$ is selected from hydrogen, an alkali-metal or an esterifying group with an alkanolamine compound of the formula:

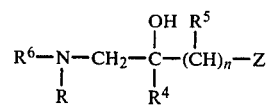

wherein Z, R, $R^4$, $R^5$ and n are as defined above and $R^6$ is hydrogen or an amine protecting group using one of the following conditions (a) or (b):

(a) firstly, reacting said alkanolamine or said alkanolamino having a protected or unprotected secondary amine function with a strong alkali-metal non-nucleophilic base, and secondly, reacting the product thereof with said aromatic compound and deprotecting the secondary amine function if present to give a compound of the formula:

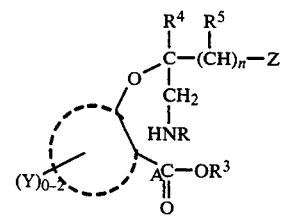

wherein A, Z, Y, R, $R^3$, $R^4$, $R^5$ and n have the starting values; or (b) reacting said aromatic compound wherein $R^3$ is an alkali-metal ion with said alkanol amine in the presence of a dehydrating agent or a condensation agent to give a compound of the formula:

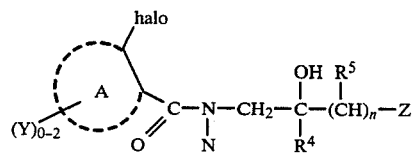

wherein A, Z, Y, $R^4$, $R^5$ and n have the starting values;

Step 2, cyclizing a compound prepared in Step 1 to give a compound of the formula:

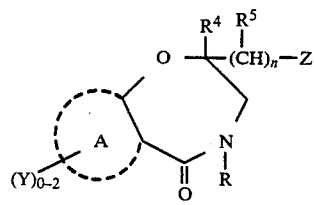

wherein A, Z, Y, R, $R^4$, $R^5$ and n have the starting values; and

Step 3, optionally, when desired, reacting a compound prepared in Step 2 with a sulfurizing agent to give a compound of the Formula:

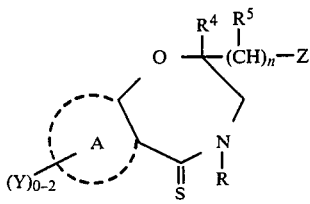

wherein Y, Z, A, R, $R^4$, $R^5$ and n have the starting values.

2. The process of claim 1 wherein the compound prepared is 2-[(dimethylamino)methyl]-2,3-dihydro-4-methylpyrido[3,2-b][1,4]oxazepin-(5(4H)-one or a pharmaceutically acceptable acid addition salt thereof.

3. The process of claim 1 wherein the compound prepared is 2-[2-(dimethylamino)ethyl]-2,3-dihydro-4-methyl-1,4-oxazepino[6,7-c]quinolin-5(4H)-one or a pharmaceutically acceptable acid addition salt thereof.

4. The process of claim 1 wherein the compound prepared is 2-[2-(dimethylamino)ethyl]-2,3-dihydropyrido[3,2-f]-1,4-oxazepin-5(4H)-one or a pharmaceutically acceptable acid addition salts thereof.

5. The process of claim 1 wherein the compound prepared is 2-[2-(dimethylamino)ethyl)-2,3-dihydropyrido[3,2-f]-1,4-oxazepin-5(4H)-thione or a pharmaceutically acceptable acid addition salt thereof.

6. The process of claim 1 wherein the compound prepared is 2-[(dimethylamino)ethyl]-2,3-dihydro-4-methylpyrido[3,2-f][1,4-oxazepine-5(4H)-thione or a pharmaceutically acceptable acid addition salt thereof.

* * * * *